(12) United States Patent
Bonnet

(10) Patent No.: US 8,529,475 B2
(45) Date of Patent: Sep. 10, 2013

(54) DEVICE FOR ANALYZING GAIT

(75) Inventor: Stephane Bonnet, Lyons (FR)

(73) Assignee: Commissariat a l'Energie Atomique, Paris (FR)

( * ) Notice: Subject to any disclaimer, the term of this patent is extended or adjusted under 35 U.S.C. 154(b) by 560 days.

(21) Appl. No.: 12/364,752

(22) Filed: Feb. 3, 2009

(65) Prior Publication Data
US 2009/0198155 A1 Aug. 6, 2009

(30) Foreign Application Priority Data

Feb. 4, 2008 (FR) ...................................... 08 00571

(51) Int. Cl.
*A61B 5/11* (2006.01)
*G01R 33/02* (2006.01)

(52) U.S. Cl.
USPC .......................................... 600/595; 324/261

(58) Field of Classification Search
USPC ........................... 428/212; 600/595; 324/261
See application file for complete search history.

(56) References Cited

U.S. PATENT DOCUMENTS

| | | | |
|---|---|---|---|
| 6,959,259 B2 * | 10/2005 | Vock et al. ..................... | 702/142 |
| 7,602,301 B1 * | 10/2009 | Stirling et al. ............. | 340/573.1 |
| 2006/0184276 A1 * | 8/2006 | Takenaka et al. ............. | 700/245 |
| 2007/0219744 A1 * | 9/2007 | Kolen ............................ | 702/150 |
| 2007/0250134 A1 * | 10/2007 | Miesel et al. ................... | 607/45 |
| 2009/0046056 A1 * | 2/2009 | Rosenberg et al. ........... | 345/156 |
| 2009/0278791 A1 * | 11/2009 | Slycke et al. .................. | 345/156 |

FOREIGN PATENT DOCUMENTS

| FR | 2 895 499 | | 6/2007 |
|---|---|---|---|
| FR | 2895499 A1 | * | 6/2007 |

OTHER PUBLICATIONS

Machine_English_Translation_Stephane_Bonnet_Estimation of the Orientation of an Object, Jun. 29, 2007, EPO, whole document.*
K Aminian; "Spatio-temporal parameters of gait measured by an ambulatory system using miniature gyroscopes"; Dec. 28, 2001; Journal of Biomechanics; 35; p. 689-699.*
R. Héliot, et al., "Continuous Identification of Gait Phase for Robotics and Rehabilitation Using Microsensors", Advanced Robotics, ICAR '05. Proceedings., 12th International Conference, XP010835347, Jul. 18-20, 2005, pp. 686-691.

(Continued)

*Primary Examiner* — David Sample
*Assistant Examiner* — Tahseen N Khan
(74) *Attorney, Agent, or Firm* — Oblon, Spivak, McClelland, Maier & Neustadt, L.L.P.

(57) ABSTRACT

A method and device for analyzing a gait of a person includes a magnetometer for fastening to a tibial segment of the person, in order to generate a signal representative of at least one projection onto a sagittal plane of an ambient magnetic field in which the magnetometer is immersed and a signal processor to identify instants and/or phases that are characteristic of the gait of the person by identifying particular points in the signal generated by the magnetometer as a function of time.

20 Claims, 2 Drawing Sheets

(56) References Cited

OTHER PUBLICATIONS

X. Yun, et al., "Self-Contained Position Tracking of Human Movement Using Small Inertial/Magnetic Sensor Modules", IEEE International Conference on Robotics and Automation, XP-002505760, 2007, 2 pages (Derwent Abstract Only).

K. J. O'Donovan, et al., "An Inertial and Magnetic Sensor Based Technique for Joint Angle Measurement", Journal of Biomechanics, The Institution of Engineering and Technology, vol. 40, No. 12, XP-002505761, Mar. 7, 2007, 1 page (Derwent Abstract Only).

Bob Kemp, et al., "Body position can be monitored in 3D using miniature accelerometers and earth-magnetic field sensors", Electroencephalography and Clinical Neurophysiology, vol. 109, XP-002367000, Dec. 1, 1998, pp. 484-488.

* cited by examiner

DEVICE FOR ANALYZING GAIT

FIELD OF THE INVENTION

The invention relates to a device for analyzing the gait of a person, and more particularly to a device suitable for identifying instants and phases that are characteristic of the gait of said person.

In particular, a device of the invention makes it possible to determine automatically the support and the flight phases for each swing of the gait. It also makes it possible to count the number of swings and as a result to estimate the cadence of the gait.

This information presents medical and paramedical interest, particularly in podology, for clinical descriptive analysis of gait and to enable functional electrical stimulation to be triggered.

BACKGROUND OF THE INVENTION

The article by K. Aminian et al. entitled "Spatio-temporal parameters of gait measured by an ambulatory system using miniature gyroscopes", Journal of Biomechanics 35 (2000), pages 689-699, describes a method of analyzing gait that makes use of at least one gyroscope fastened to a person's "shank" or tibial segment. A comparison with signals acquired by pressure-sensitive switches fastened to the heel and to the big toe shows that measuring the angular velocity of the tibial segment, as performed by means of a gyroscope, makes it possible to identify two characteristic instants of the swing: the moment when the toe leaves the ground (TO, for "toe-off"), and the moment when the heel strikes the ground (HS, for "heel-strike"). The period lying between the instants TO and HS corresponds to the flight phase of the swing for the leg under consideration; conversely, the period extending between the instants HS and TO corresponds to the support phase.

The drawback of the device proposed by K. Aminian et al. is associated with using gyroscopes, which are devices that are relatively bulky (and therefore uncomfortable for the person) and that consume a large amount of electricity.

The use of pressure-sensitive switches, also disclosed in the above-mentioned article, gives information only about the support phase and not about the flight phase of the swing.

Document EP 1 721 573 describes a method of estimating the phase of the movement of an object, which method includes acquiring experimental data from measuring physical magnitudes by means of at least one sensor. In particular, that document mentions determining the heel strike (HS instant) by analyzing an acceleration signal. The main drawback of that method is its computational complexity. Furthermore, accelerometers are sensitive to the inseparable combination of acceleration due to gravity and acceleration of the sensor. This presents high frequency components that make it difficult to determine the direction of acceleration due to gravity.

The article by S. Bonnet and R. Héliot entitled "A magnetometer-based approach for studying human movements", published in IEEE Transactions on Biomedical Engineering, Vol. 54, No. 7, July 2007, pages 1353-1355, describes a method making it possible to study the inclination of the torso with the help of magnetometers. In particular, by assuming that motion is planar, it is possible to determine the angle formed by the torso relative to the vertical. Nevertheless, the processing of the data is complex (minimizing a cost function relative to two variables). In addition, the document does not give any indication on how it might be possible to use the information as obtained in that way to identify instants and phases that are characteristic of a person's gait.

Document FR 2 895 499 describes a method of measuring the orientation of a solid with the help of a magnetometer, and also an application thereof to determining the orientation of the thigh and the tibia of a leg while walking, from which it is possible to deduce the angle of the knee. Identifying instants and/or phases that are characteristic of gait is neither described nor suggested.

The article by R. Héliot et al. entitled "Continuous identification of gait phase for robotics and rehabilitation using microsensors", published in Proceedings of the International Conference on Advanced Robotics, 2005—ICAR '05, describes a method of determining gait phases from orientation measurements of the tibia and of the thigh performed with the help of respective sensors, comprising accelerometers and magnetometers, which method requires complex data processing.

OBJECT AND BRIEF SUMMARY OF THE INVENTION

The invention seeks to solve at least some of the drawbacks of the prior art by providing a gait analysis device that is simple in terms of its mechanical structure and in terms of the data processing method it implements.

Advantageously, the device of the invention is simple and flexible to use, since it makes use of the Earth's magnetic field, which is naturally available everywhere. The person need not necessarily walk in a determined direction, nor even in a straight line.

Magnetometers are sensors of small dimensions that consume little electricity, so wearing the device of the invention presents little discomfort.

In accordance with the invention, at least one of the above-mentioned objects can be achieved with the help of a device for analyzing the gait of a person, wherein the device comprises:

a magnetometer for fastening to a tibial segment of said person, in order to generate a signal representative of at least one projection onto a sagittal plane of an ambient magnetic field in which it is immersed; and signal processor means for identifying instants and/or phases that are characteristic of the gait of said person from the signal generated by said magnetometer.

According to particular embodiments of the invention:

Said signal processor means may be adapted to identify characteristic instants of the person's gait by identifying particular points in the expression as a function of time for said signal generated by said magnetometer.

More particularly, said signal processor means may be adapted to identify characteristic instants of the person's gait by identifying local extrema in the expression as a function of time for the angle formed by said projection onto a sagittal plane of the ambient magnetic field, relative to the vertical.

In a variant, said signal processor means may be adapted to identify characteristic instants of the person's gait by identifying local extrema in the expression as a function of time for the time derivative of the angle formed relative to the vertical by said projection onto a sagittal plane of the ambient magnetic field.

In another variant, said signal processor means may be adapted to identify characteristic instants of the person's gait by identifying local extrema in the expression as a function of time for a component that is substantially perpendicular to the person's tibial segment of said projection onto a sagittal plane of the ambient magnetic field.

Said magnetometer may be a three-axis magnetometer.

Under such circumstances, said processor means may also be adapted to determine the gait heading from a signal representative of at least one medio-lateral component of said ambient magnetic field, likewise generated by said magnetometer.

Said processor means may also be adapted to receive to receive as input calibration information indicative of the inclination of said ambient magnetic field relative to the vertical, and to make use of said calibration information in order to determine the angle between said tibial segment and the vertical axis at said characteristic instants of the person's gait.

The device may also include a second magnetometer adapted to be fastened to a thigh of the person, said magnetometer being adapted to generate a second signal representative of at least one projection onto a sagittal plane of an ambient magnetic field in which it is immersed; wherein said signal processor means is also adapted to determine a flexing angle of the person's knee from the signal generated by said magnetometers.

The invention also provides the use of a device as defined above to identify instants and phases that are characteristic of a person's gait, said person being immersed solely in the Earth's magnetic field and said magnetometer being fastened to a tibial segment of said person with an orientation that is at least approximately known relative to the person's sagittal plane.

BRIEF DESCRIPTION OF THE DRAWINGS

Other characteristics, details, and advantages of the invention appear on reading the description made with reference to the accompanying drawings, in which.

Figure 6A:
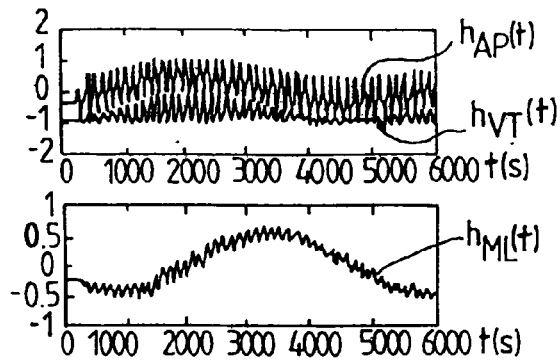
FIGS. 6A to 6D show various signals generated by the magnetometer and how they are used for identifying characteristic instants and phases of gait.
Figure 6B:
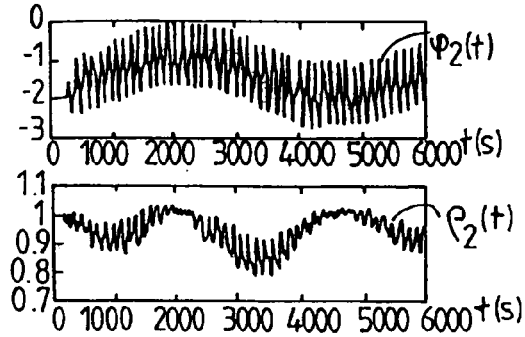
Figure 6C:
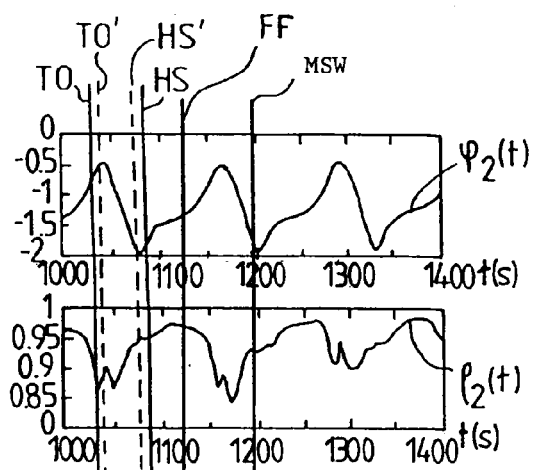
Figure 6D:
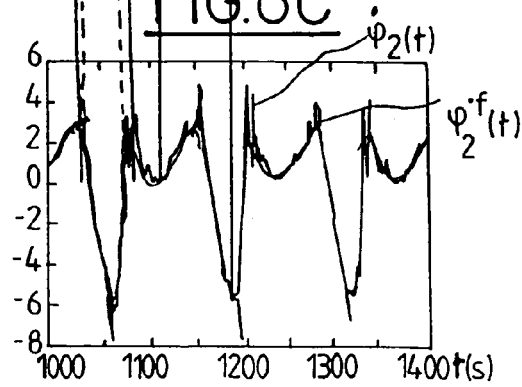
Figure 7:
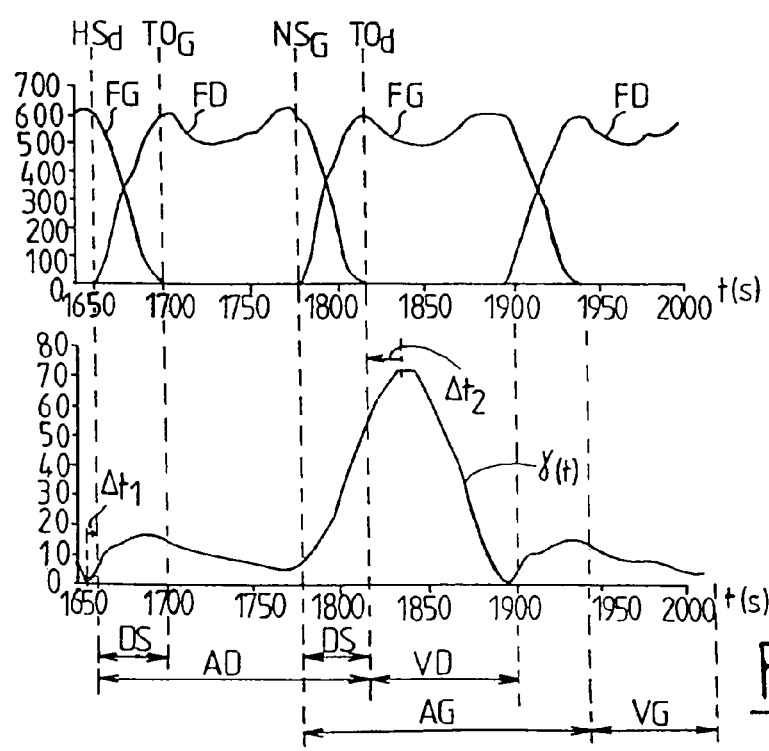
FIG. 7 shows the use of a measurement of the knee flexing angle for identifying characteristic instants and phases of gait.

In the graphs of FIGS. 6A to 7, the abscissa axis represents time, expressed in seconds. The units on the ordinate axis are arbitrary.

MORE DETAILED DESCRIPTION

Figure 1:
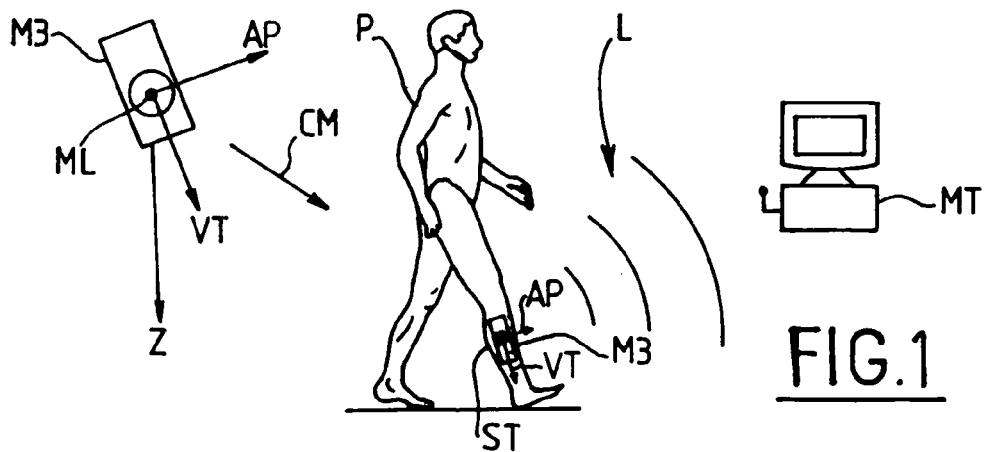
FIG. 1 shows a device of the invention in use.

As shown in FIG. 1, the device of the invention comprises a three-axis magnetometer M3 suitable for fastening to a tibial segment ST of a person P, together with signal processor means connected to said magnetometer via a link L, e.g. a wireless link. In the example shown in the figure, the processor means MT comprise an office computer, but they could equally well be constituted by a portable device attached to the person's body or clothing. The link L serves to transmit to the processor means MT signals that are generated by the magnetometer M3, which magnetometer, like the person, is immersed in an ambient magnetic field, typically in the Earth's magnetic field, represented by a vector CM in the figure. The link L need not necessarily be implemented in real time: it is possible to provide means for recording the signals from the magnetometer in order to perform analysis "offline".

The measurement axes of the magnetometer M3 are assumed to be mutually orthogonal and they are identified by references VT, AP, and ML. The axis VT (for "vertical") is parallel to the tibial segment, and is oriented downwards; in spite of its name, it does not remain vertical while the person is walking. The axis AP (for "antero-posterior") is oriented towards the front, while the axis ML (for "medio-lateral") is oriented laterally. While walking, it can be assumed that the axis ML remains horizontal and lies in the frontal plane PF of the person's body, while the axes AP and VT turn in the sagittal plane PS.

Figure 2:
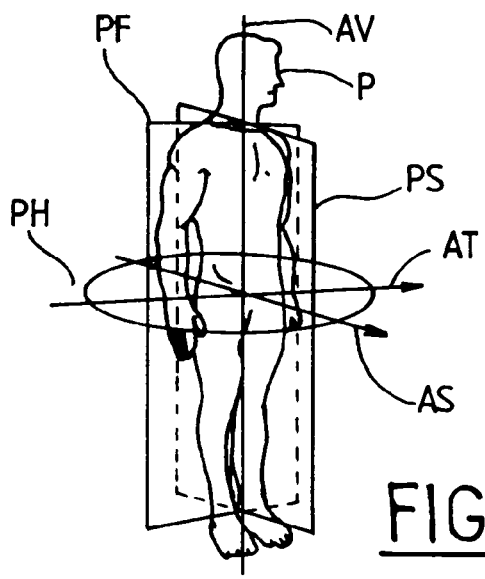
FIG. 2 shows the anatomical planes of the human body.

The anatomical planes of the human body (horizontal plane PH; frontal plane PF; sagittal plane PS), and the vertical, sagittal, and transverse axes AV, AS, and AT are shown in FIG. 2.

The invention is not limited to circumstances in which the ambient magnetic field is the Earth's magnetic field; nevertheless, that constitutes a preferred implementation of the invention since the magnetic field is present everywhere, and is substantially uniform at the scale at which the invention is implemented, with its inclination being known, at least approximately.

Figure 3:
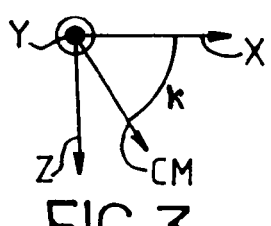
FIG. 3 shows the Earth's magnetic field in the geophysical inertial frame of reference.

FIG. 3 shows the vector of the Earth's magnetic field CM in an inertial rectangular frame of reference XYZ in which:
the axis Z points downwards (local vertical);
the axis X is horizontal and points to magnetic north; and
the axis Y is horizontal and points to the east.

The magnetic field CM points to magnetic north (by definition of magnetic north), and forms an angle $\kappa$ with the axis X. The inclination $\kappa$ of the magnetic field CM relative to the horizontal depends on location (and is about 60° in France), but it may be considered as being constant, locally. Assuming that its magnitude is normalized as 1, the magnetic field CM is expressed in the inertial frame of reference XYZ as follows:

$$h_i = \begin{pmatrix} \cos\kappa \\ 0 \\ \sin\kappa \end{pmatrix}$$

Figures 4A, 4B:
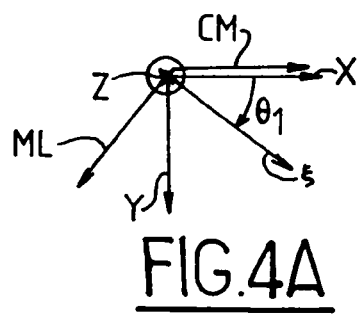
FIGS. 4A and 4B are projections of the Earth's magnetic field onto the sagittal plane of the FIG. 2 human body.

The magnetic field CM may also be expressed in the moving frame of reference of the sensor (AP, ML, VT). In FIGS. 4A and 4B, the vector $\xi$ indicates the gait direction, characterized by an azimuth direction (relative to magnetic north) $\theta_1$, and the plane (Z, $\xi$) coincides with the sagittal plane PS of the body. Ideally, the axis AP of the magnetometer is aligned with the gait direction $\xi$.

In FIG. 4B, the vector CMS represents the projection onto the sagittal plane (Z, $\xi$) of the magnetic field CM. This vector forms an angle $\phi_1$ with the vertical (axis Z). It is important to observe that in general $\phi_1 \neq \kappa$.

In the plane (Z, $\xi$), the vector CMS may be expressed as follows:

$$\begin{pmatrix} \sin\kappa \\ \cos\theta_1 \cos\kappa \end{pmatrix} = \rho_1 \begin{pmatrix} \cos\varphi_1 \\ \sin\varphi_1 \end{pmatrix}$$

The norm $\rho_1$ of this vector depends both on $\kappa$ and on the heading of the walker, $\theta_1$.

While walking, the axes AP and VT of the magnetometer turn in the sagittal plane, while the axis ML remains stationary and perpendicular to said plane. Let $\theta_2$ be the angle of inclination of the person's tibial segment relative to the vertical, or equivalently, the angle between the axis VT and the vertical, or the angle lying between the axis AP and the horizontal. A convention is used whereby the angle $\theta_2$ is positive when the tibial segment is oriented rearwards (i.e., in particular, at instant "TO" when the toe leaves the ground).

In completely general manner, the vector CMS (projection onto the sagittal plane of the Earth's magnetic field) can be expressed by its components along the axes of the magnetometer, $h_{AP}$ and $h_{VT}$, or in polar coordinates ($\rho_2$, $\phi_2$), as follows:

$$\begin{pmatrix} h_{VT} \\ h_{AP} \end{pmatrix} = \rho_2 \begin{pmatrix} \cos\varphi_2 \\ \sin\varphi_2 \end{pmatrix}$$

The phase $\phi_2$ of the expression for the vector CMS In polar coordinates is defined in such a manner that $\phi_2=0$ when it is oriented parallel to the axis of the tibial segment, i.e. when the vector CMS is parallel to the axis VT. In other words, $\phi_2$ represents the angle formed by the projection onto the sagittal plane PS of the ambient magnetic field CM relative to the axis VT.

Figure 5A:
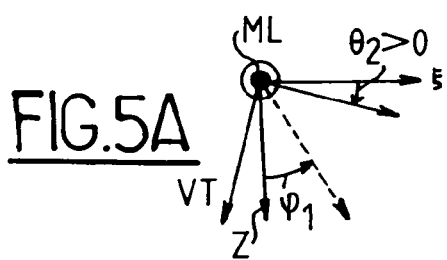
FIGS. 5A and 5B show how the angle of inclination of the magnetometer (and thus of the tibial segment) is determined relative to the vertical.
Figure 5B:
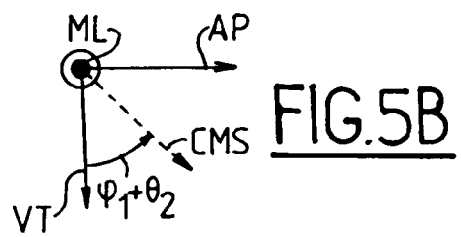

FIGS. 5A and 5B show that:

$$\begin{cases} \rho_2 = \rho_1 \\ \varphi_2 = \theta_2 + \varphi_1 \end{cases}$$

The second of these equations shows that the phase $\phi_2$ is equal to the angle of the tibial segment $\theta_1$ plus an offset $\phi_1$ that depends on $\kappa$ and on the heading $\theta_1$ of the walker. Since $\kappa$ is uniform locally, if the person is walking in a straight line (constant heading), then the offset $\phi_1$ is constant.

The idea on which the invention is based is that knowing the angle $\phi_2$ and how it varies in time makes it possible to determine the characteristic instants and phases of gait, even if the heading of the walker is not constant.

FIG. 6A shows graphs of the three components of the magnetic field CM as measured by the magnetometer M3 when walking in a circle: $h_{AP}(t)$, $h_{VT}(t)$ in the upper diagram, and $h_{ML}(t)$ in the lower diagram. In theory, under such conditions, $h_{ML}(t)$ should follow a sinusoidal relationship. The high frequency components visible in the figure are due to imperfect alignment of the magnetometer axis ML with the transverse axis of the person.

FIG. 6B plots the polar components of the vector CMS: in the upper diagram, the phase $\phi_2(t)$; and in the lower diagram, the norm $\rho_2(t)$. As explained above, these magnitudes can be obtained from the measured values $h_{AP}(t)$, $h_{VT}(t)$ by using the above-mentioned equation:

$$\begin{pmatrix} h_{VT} \\ h_{AP} \end{pmatrix} = \rho_2 \begin{pmatrix} \cos\varphi_2 \\ \sin\varphi_2 \end{pmatrix}$$

FIG. 6C shows a detail of FIG. 6B.

FIG. 6D is a plot of the time derivative of $\phi_2(t)$, written $\dot{\phi}_2(t)$ together with a filtered version thereof $\dot{\phi}_2^f(t)$ (lowpass filter). The plots of FIGS. 6C and 6D are aligned.

It can be seen that the plots of $\dot{\phi}_2(t)$ and of $\dot{\phi}_2^f(t)$ are very similar to the plot of the angular speed of the tibial segment as reproduced in the above-mentioned article by K. Aminian et al. It is thus possible to identify remarkable points of the curve $\dot{\phi}_2^f(t)$ (which is easier to use than $\dot{\phi}_2(t)$ since the curve is smoother) and to associate them with the instants TO and HS that split up the gait cycle. These remarkable points are the maximum points of $\dot{\phi}_2^f(t)$; if an opposite time convention is selected, they would then be the minimum points.

Since the maxima of $\dot{\phi}_2^f(t)$ are very narrow, the maximum points are very close in time to zero crossings, which in turn correspond to extremum points of the curve representing $\phi_2(t)$. Consequently, as shown in FIGS. 6C and 6D, the characteristic instants of gait TO' and HS' can be determined approximately directly by identifying the extrema of $\phi_2(t)$. The instants TO' and HS' present an offset relative to the instants TO and HS as determined from the plot of $\dot{\phi}_2^f(t)$. This offset may be estimated by calibration, but as a general rule using the derivative $\dot{\phi}_2^f(t)$ provides more accurate results.

Other remarkable instants of gait phase, the mid-swing instant (MSW) and the foot flat (FF) instant can be identified from the curve $\dot{\phi}_2^f(t)$. In the time convention used in FIG. 6D, these points correspond to the minima, in $\dot{\phi}_2^f(t)$ respectively a main minimum and a secondary minimum. Unlike the instants TO and HS, the instants MSW and FF are difficult to identify from the curve $\phi_2(t)$ of FIG. 6C.

At the moment the heel strikes the ground, the leg is practically extended, so the angle of the knee is very small. The foot makes contact (HS), and the knee bends to absorb the impact until the end of the double support phase, the knee reaches a first local flexing maximum, the foot is flat on the ground (instant FF). The leg then extends to apply thrust and the body passes onto the other leg for the second double support phase. During this second double support phase, the knee bends until the toes leave the ground (TO) and continues flexing during the beginning of the oscillating phase so as to enable it to pass in front of the body. The knee then reaches a second local flexing maximum at the mid-swing (MSW) instant.

At instant FF, the foot presses flat against the ground, the tibia is oriented vertically, and the speed and the acceleration of the foot are zero at this instant.

Thus, by having a device as described by the invention on each of an individual's legs, it is possible to know the four characteristic instants (TO, MS, FF, HS) corresponding to each leg, as a function of time. This makes it possible to analyze the gait model well.

Remarkable points can be searched for in $\phi_2(t)$ or $\dot{\phi}_2^f(t)$ automatically by techniques known in the prior art. In general, whatever the sign convention adopted, it is possible to determine MS, FF, TO, and HS from the curve of $\dot{\phi}_2^f(t)$, these points correspondingly respectively:

- to each extremum of greatest amplitude in absolute value (or main extremum)→MSW;
- to each extremum of the same sign as a main extremum, immediately preceding (or following) said main extremum→FF;
- to the extremum of sign opposite to the main extremum preceding said main extremum→TO; and
- to the extremum of sign opposite to the main extremum following said main extremum→HS.

This description is quite universal in the context of normal gait, however there can be variants for pathological gaits.

The curve for $\dot{\phi}_2^f(t)$ shows that the gait cycle is periodic, with the period being defined as the time interval between two successive identical characteristic instants.

It can be particularly useful to identify the instant FF in order to determine the heading and the path of the gait. At this instant, the tibial segment of the leg is substantially vertical.

Thus, if the axis VT of the accelerometer is in good alignment with said tibial segment, then the two axes AP and ML lie in a horizontal plane and enable the heading of the gait to be determined relative to magnetic north.

In addition, in correspondence with the same instant FF, the acceleration and the speed of the tibial segments are zero. If an auxiliary accelerometer is provided on the tibia, this information serves to calculate the gait path by double integration of the signal delivered by said accelerometer.

In a variant, it is possible to determine at least some characteristic points of gait (HS and TO, and with greater difficulty MSW and FF) directly from the plot of $h_{AP}(t)$. This is because $$h_{AP}(t) \propto \sin \phi_2 \approx \phi_2$$

The accuracy of this alternative method is nevertheless not so good. In any event, it is preferable to begin by eliminating the "base line" of the curve representing $h_{AP}(t)$, due to changes of gait heading. This base line is clearly visible in FIG. 6A, where it presents a sinusoidal appearance due to the fact that the person is following a circular path.

By providing a second magnetometer secured to the person's thigh, and by applying signal processing equivalent to that described above, it is possible to determine the angle of inclination $\psi$ of the person's femur, to within an offset $\phi_1$. Subtracting the femur angle $\psi$ from the angle $\phi_2$ of the tibial segment gives the flexing angle $\gamma$ of the knee. It is advantageous to observe that this subtraction serves to eliminate the offset $\phi_1$ directly.

Measuring the knee angle $\gamma$ (t) is itself advantageous for medical and paramedical purposes. Furthermore, the characteristic instants and phases of gait can also be determined from the plot of $\gamma(t)$, or from its time derivative, as shown in FIG. 7. This figure plots the angle of the right knee $\gamma(t)$ in association with the vertical components of the ground reaction forces (FD and FG for the right and left feet respectively), as measured using a mat fitted with sensors. The offsets $\Delta t_1$, $\Delta t_2$ between the "true" instants HS and TO and the corresponding extrema in $\gamma(t)$ can be determined by calibration.

In FIG. 7, there can be seen the gait phases as defined by the characteristic instants HS and TO: double support (DS), right support (AD), right flight (VD), left support (AG), and left flight (VG).

Another parameter of interest made accessible by the invention is the angle of inclination of the tibial segment relative to the vertical, $\theta_2$. In particular, it is useful to know its value (or "angle of attack") at the moment the heel strikes the ground, HS. Since $$\theta_2 = \phi_2 - \phi_1$$

and $\phi_1$ depends both on $\theta_1$ and on $\kappa$, which angle is known to a good approximation, it is necessary to determine the heading $\theta_1$. A first possibility consists in performing a trignometrical calculation on the component ML of the magnetometer signal:

$$h_{ML} = -\sin \theta_1 \cos \kappa$$

A variant consists in calculating the arc-tangent of $h_{ML}/h_{AP}$ using only signals measured during the support phase, when the tibial segment is approximately perpendicular relative to the ground. This variant presents the advantage of not depending on accurate knowledge of the angle $\kappa$.

What is claimed is:

1. A device for analyzing a gait of a person, the device comprising:
   a magnetometer for fastening to a tibial segment of said person, in order to generate a signal representative of at least one projection onto a sagittal plane of an ambient magnetic field in which the magnetometer is immersed; and
   signal processor means for identifying instants that are characteristic of the gait of said person solely by identifying particular points in the signal generated by the magnetometer as a function of time,
   wherein said instants that are characteristic of the gait of said person comprise at least one selected from a group including a toe-off and a heel-strike instant.

2. A device according to claim 1, wherein said signal processor means is adapted to identify the characteristic instants of the person's gait by identifying local extrema in the signal generated by the magnetometer as a function of time for an angle formed by said projection onto the sagittal plane of the ambient magnetic field relative to said tibial segment.

3. A device according to claim 1, wherein said signal processor means is adapted to identify the characteristic instants of the person's gait by identifying local extrema in the signal generated by the magnetometer as a function of time for a component that is substantially perpendicular to the person's tibial segment of said projection onto the sagittal plane of the ambient magnetic field.

4. A device according to claim 1, wherein said processor means is also adapted to receive as input calibration information indicative of an inclination of said ambient magnetic field relative to a vertical direction of the tibial segment, and to determine an angle between said tibial segment and a vertical axis at said characteristic instants of the person's gait based on said calibration information.

5. A device according to claim 1, further comprising a second magnetometer adapted to be fastened to a thigh of the person, said second magnetometer being adapted to generate a second signal representative of at least one projection onto the sagittal plane of the ambient magnetic field in which the second magnetometer is immersed;
   wherein said signal processor means is also adapted to determine a flexing angle of a knee of the person from the signal generated by said magnetometers.

6. A device according to claim 1, wherein the signal processor means is a computer.

7. A device according to claim 1, wherein the ambient magnetic field is the Earth's magnetic field.

8. A device according to claim 1, wherein said instants that are characteristic of the gait of said person comprise the toe-off instant and the heel-strike instant.

9. A device according to claim 1, wherein said signal processor means is adapted to identify the characteristic instants of the person's gait by identifying local extrema in the signal generated by the magnetometer as a function of time for a time derivative of an angle formed, relative to said tibial segment, by said projection onto the sagittal plane of the ambient magnetic field.

10. A device according to claim 9, wherein the local extrema identified by the signal processor means include
   a first extreme to identify a mid-swing instant of the gait, the first extreme being greatest amplitude in absolute value of the extrema,
   a second extreme to identify a flat foot instant of the gait, the second extreme being a same sign and immediately preceding or following the first extreme of the extrema,
   a third extreme to identify the toe-off instant of the gait, the third extreme being a sign opposite to and immediately preceding the first extreme of the extrema, and
   a fourth extreme to identify the heel-strike instant of the gait, the fourth extreme being a sign opposite to and immediately following the first extreme of the extrema.

11. A device according to claim 1, wherein said magnetometer is a three-axis magnetometer.

12. A device according to claim 11, wherein said processor means is also adapted to determine a gait heading from a signal representative of at least one medio-lateral component of said ambient magnetic field, the signal representative of at least one medio-lateral component being generated by said magnetometer.

13. A method of analyzing a gait of a person, comprising:
fastening a magnetometer to a tibial segment of the person to generate a signal representative of at least one projection onto a sagittal plane of an ambient magnetic field in which the magnetometer is immersed; and
identifying instants that are characteristic of the gait of said person solely by identifying particular points in the signal generated by the magnetometer as a function of time,
wherein said instants that are characteristic of the gait of said person comprise at least one selected from a group including a toe-off and a heel-strike instant.

14. A method according to claim 13, wherein the identifying includes identifying the characteristic instants of the person's gait by identifying local extrema in the signal generated by the magnetometer as a function of time for an angle formed by said projection onto the sagittal plane of the ambient magnetic field relative to said tibial segment.

15. A method according to claim 13, wherein the identifying includes identifying the characteristic instants of the person's gait by identifying local extrema in the signal generated by the magnetometer as a function of time for a component that is substantially perpendicular to the person's tibial segment of said projection onto the sagittal plane of the ambient magnetic field.

16. A method according to claim 13, wherein the identifying includes determining a gait heading from a signal representative of at least one medio-lateral component of said ambient magnetic field, the signal representative of at least one medio-lateral component being generated by said magnetometer.

17. A method according to claim 13, wherein the identifying includes receiving as input calibration information indicative of an inclination of said ambient magnetic field relative to a vertical direction of the tibial segment, and determining an angle between said tibial segment and a vertical axis at said characteristic instants of the person's gait based on said calibration information.

18. A method according to claim 13, wherein said instants that are characteristic of the gait of said person comprise the toe-off instant and the heel-strike instant.

19. A method according to claim 13, wherein the identifying includes identifying the characteristic instants of the person's gait by identifying local extrema in the signal generated by the magnetometer as a function of time for a time derivative of an angle formed, relative to said tibial segment, by said projection onto the sagittal plane of the ambient magnetic field.

20. A method according to claim 19, wherein the local extrema identified by the signal processor means include
a first extreme to identify a mid-swing instant of the gait, the first extreme being greatest amplitude in absolute value of the extrema,
a second extreme to identify a flat foot instant of the gait, the second extreme being a same sign and immediately preceding or following the first extreme of the extrema,
a third extreme to identify the toe-off instant of the gait, the third extreme being a sign opposite to and immediately preceding the first extreme of the extrema, and
a fourth extreme to identify the heel-strike instant of the gait, the fourth extreme being a sign opposite to and immediately following the first extreme of the extrema.

* * * * *